United States Patent
Kulshrestha et al.

(10) Patent No.: US 9,718,949 B2
(45) Date of Patent: Aug. 1, 2017

(54) RECYCLED RESIN COMPOSITIONS AND DISPOSABLE MEDICAL DEVICES MADE THEREFROM

(71) Applicant: Becton, Dickinson and Company, Franklin Lakes, NJ (US)

(72) Inventors: Ankur S. Kulshrestha, Hillsborough, NJ (US); Mildred Calistri-Yeh, Florham Park, NJ (US); Lourdes Pia Lopez Amora, Glenview, IL (US); Richard Giddes, Edison, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/685,930

(22) Filed: Apr. 14, 2015

(65) Prior Publication Data

US 2015/0218354 A1    Aug. 6, 2015

Related U.S. Application Data

(63) Continuation of application No. 12/859,972, filed on Aug. 20, 2010, now abandoned.

(51) Int. Cl.
| | |
|---|---|
| *C08L 23/12* | (2006.01) |
| *A61L 31/04* | (2006.01) |
| *B29C 45/00* | (2006.01) |
| *A61L 29/04* | (2006.01) |
| *A61L 29/14* | (2006.01) |
| *A61L 31/14* | (2006.01) |
| *B29C 47/54* | (2006.01) |
| *B29K 23/00* | (2006.01) |
| *B29L 31/00* | (2006.01) |

(52) U.S. Cl.
CPC .............. *C08L 23/12* (2013.01); *A61L 29/04* (2013.01); *A61L 29/14* (2013.01); *A61L 31/04* (2013.01); *A61L 31/048* (2013.01); *A61L 31/14* (2013.01); *B29C 45/0001* (2013.01); *B29C 47/54* (2013.01); *B29K 2023/12* (2013.01); *B29L 2031/753* (2013.01)

(58) Field of Classification Search
CPC .. C08L 23/12; C08L 2207/20; C08L 2666/78; A61L 29/04
USPC .............. 521/40; 523/105; 524/500; 525/50
See application file for complete search history.

(56) References Cited

U.S. PATENT DOCUMENTS

| | | |
|---|---|---|
| 4,495,312 A | 1/1985 | Hata et al. |
| 4,959,402 A | 9/1990 | Williams et al. |
| 4,994,552 A | 2/1991 | Williams et al. |
| 5,075,057 A | 12/1991 | Hoedl |
| 5,129,884 A | 7/1992 | Dysarz |
| 5,226,897 A | 7/1993 | Nevens |
| 5,271,500 A | 12/1993 | Szacon |
| 5,277,869 A | 1/1994 | Glazer et al. |
| 5,328,484 A | 7/1994 | Somers et al. |
| 5,350,562 A | 9/1994 | Anthony |
| 5,356,948 A | 10/1994 | Payne, Jr. et al. |
| 5,395,681 A | 3/1995 | Hargarter et al. |
| 5,427,737 A | 6/1995 | Glazer et al. |
| 5,462,794 A | 10/1995 | Lindemann et al. |
| 5,508,004 A | 4/1996 | Held et al. |
| 5,520,642 A | 5/1996 | Bigagli et al. |
| 5,557,905 A | 9/1996 | Harding |
| 5,558,280 A | 9/1996 | Morgan |
| 5,582,793 A | 12/1996 | Glazer et al. |
| 5,645,603 A | 7/1997 | Peters |
| 5,686,527 A | 11/1997 | Laurin et al. |
| 5,693,026 A | 12/1997 | Spinello |
| 5,693,278 A | 12/1997 | Clements |
| 5,785,260 A | 7/1998 | Morgan |
| 5,824,745 A | 10/1998 | Brown |
| 5,830,396 A | 11/1998 | Higgins et al. |
| 5,833,922 A | 11/1998 | Held et al. |
| D412,206 S | 7/1999 | Basile et al. |
| 5,986,002 A | 11/1999 | Hwang et al. |
| 5,998,019 A | 12/1999 | Rosenbaum et al. |
| 6,004,297 A | 12/1999 | Steenfeldt-Jensen et al. |

(Continued)

FOREIGN PATENT DOCUMENTS

| | | |
|---|---|---|
| DE | 4319989 | 12/1994 |
| DE | 19726105 | 12/1998 |
| EP | 0665327 | 8/1995 |
| EP | 1702637 | 9/2006 |
| EP | 2000164 | 12/2008 |
| JP | H10-036598 A | 2/1998 |
| JP | H10-067894 A | 3/1998 |
| JP | H11-291247 | 10/1999 |
| JP | H11-291247 A | 10/1999 |
| JP | 2000-005283 | 1/2000 |

(Continued)

OTHER PUBLICATIONS

Polypropylene. 12 pages, Downloaded from Wikipedia.com on Mar. 14, 2016.*
Polyethylene terephtahlate, 18 pages, Downloaded from Wikipedia.com on Mar. 14, 2016.*

(Continued)

*Primary Examiner* — Tae H Yoon
(74) *Attorney, Agent, or Firm* — Sevilla Whitney LLC

(57) ABSTRACT

Compositions including recycled resin components and medical devices and components made form such compositions are disclosed. The compositions and medical devices are characterized as biocompatible and sterilization stable. In one or more embodiments, the compositions include a recycled resin component and may include one or more of an anti-oxidant component, slip additive component, anti-static component, impact modifier component, colorant component, acid scavenger component, X-ray fluorescence agent component, radio opaque filler component, surface modifier component, melt stabilizer component, clarifier component, processing aid component and reinforcing agent component. Methods of forming medical articles and components are also disclosed.

7 Claims, 2 Drawing Sheets

(56) References Cited

U.S. PATENT DOCUMENTS

| | | | |
|---|---|---|---|
| 6,053,314 | A | 4/2000 | Pittman |
| 6,168,862 | B1 | 1/2001 | Rosenbaum et al. |
| 6,242,525 | B1 | 6/2001 | Raetzsch |
| 6,261,655 | B1 | 7/2001 | Rosenbaum et al. |
| 6,293,856 | B1 | 9/2001 | Hertz et al. |
| 6,297,322 | B1 | 10/2001 | Ding et al. |
| 6,319,976 | B1* | 11/2001 | DeNicola, Jr. ........ C08F 255/00 523/212 |
| 6,348,272 | B1 | 2/2002 | Haveaux |
| 6,391,008 | B1 | 5/2002 | Tsai |
| 6,402,721 | B1 | 6/2002 | Lo |
| 6,410,607 | B1 | 6/2002 | Ekart et al. |
| 6,416,323 | B1 | 7/2002 | Grenfell et al. |
| 6,461,696 | B1 | 10/2002 | Ling et al. |
| 6,478,780 | B1 | 11/2002 | Shields |
| 6,500,129 | B1 | 12/2002 | Mahurkar |
| 6,712,207 | B2 | 3/2004 | Panek, Jr. et al. |
| 6,746,738 | B1 | 6/2004 | Le Roy et al. |
| 6,764,465 | B2 | 7/2004 | Chen |
| 6,792,662 | B2 | 9/2004 | Samuel |
| 6,808,820 | B2 | 10/2004 | Lee et al. |
| 6,878,131 | B2 | 4/2005 | Novacek et al. |
| 6,881,493 | B2 | 4/2005 | Haveaux et al. |
| 6,881,790 | B1 | 4/2005 | Laurin |
| 6,924,013 | B1 | 8/2005 | Jammet et al. |
| 6,946,495 | B2 | 9/2005 | Zwynenburg et al. |
| 6,997,904 | B2 | 2/2006 | Sculati |
| 7,191,777 | B2 | 3/2007 | Brand et al. |
| 7,226,956 | B2 | 6/2007 | Wilkes et al. |
| 7,243,792 | B2 | 7/2007 | Panek, Jr. et al. |
| 7,531,226 | B2 | 5/2009 | Lee et al. |
| 7,592,408 | B2 | 9/2009 | Wilson, Jr. et al. |
| 7,596,844 | B2 | 10/2009 | Japuntich et al. |
| 7,600,639 | B2 | 10/2009 | Japuntich et al. |
| 7,763,675 | B2 | 7/2010 | Jarus et al. |
| 7,877,849 | B2 | 2/2011 | Panek, Jr. et al. |
| 7,918,821 | B2 | 4/2011 | Mahurkar |
| 8,268,913 | B2* | 9/2012 | Li ........................ C08J 5/18 428/339 |
| 2001/0056259 | A1 | 12/2001 | Skinkle et al. |
| 2002/0113333 | A1* | 8/2002 | Liu ..................... C08J 11/16 264/83 |
| 2003/0038046 | A1 | 2/2003 | Panek, Jr. et al. |
| 2003/0040701 | A1 | 2/2003 | Dalmose |
| 2003/0213714 | A1 | 11/2003 | Moats et al. |
| 2004/0099555 | A1 | 5/2004 | Panek, Jr. et al. |
| 2004/0235970 | A1 | 11/2004 | Smith et al. |
| 2005/0121343 | A1 | 6/2005 | Miller et al. |
| 2005/0165165 | A1* | 7/2005 | Zwynenburg .......... C08J 9/0061 525/88 |
| 2005/0192534 | A1 | 9/2005 | Wolbring et al. |
| 2005/0218142 | A1 | 10/2005 | Finnestad et al. |
| 2005/0228682 | A1 | 10/2005 | Firestone, III |
| 2006/0154350 | A1 | 7/2006 | Kolbakov et al. |
| 2006/0161106 | A1 | 7/2006 | Wu |
| 2007/0016145 | A1 | 1/2007 | Berler |
| 2007/0068832 | A1 | 3/2007 | Anderson et al. |
| 2007/0068834 | A1 | 3/2007 | Smudde et al. |
| 2007/0069490 | A1 | 3/2007 | Japuntich et al. |
| 2007/0078402 | A1 | 4/2007 | Yang |
| 2007/0100088 | A1 | 5/2007 | Gallucci et al. |
| 2007/0138689 | A1* | 6/2007 | Bravo ................ B29C 47/0004 264/211 |
| 2007/0299307 | A1* | 12/2007 | Lew ..................... A61M 5/322 600/110 |
| 2008/0058736 | A1 | 3/2008 | Reshamwala |
| 2008/0065027 | A1 | 3/2008 | Sharp |
| 2008/0067093 | A1 | 3/2008 | Japuntich et al. |
| 2008/0067094 | A1 | 3/2008 | Japuntich et al. |
| 2008/0067100 | A1 | 3/2008 | Japuntich et al. |
| 2008/0073231 | A1 | 3/2008 | Clayton et al. |
| 2008/0073232 | A1 | 3/2008 | Reshamwala et al. |
| 2008/0073251 | A1 | 3/2008 | Reshamwala et al. |
| 2008/0076879 | A1 | 3/2008 | Resemdes et al. |
| 2008/0140032 | A1 | 6/2008 | O'Malley |
| 2008/0183140 | A1 | 7/2008 | Paproski et al. |
| 2009/0032423 | A1 | 2/2009 | Japuntich |
| 2009/0048560 | A1 | 2/2009 | Caizza et al. |
| 2009/0068412 | A1 | 3/2009 | Nahmias et al. |
| 2009/0076450 | A1 | 3/2009 | Caizza et al. |
| 2009/0111719 | A1 | 4/2009 | Stoll et al. |
| 2009/0120821 | A1 | 5/2009 | Japuntich et al. |
| 2009/0131869 | A1 | 5/2009 | Caizza et al. |
| 2009/0145901 | A1 | 6/2009 | Finnestad et al. |
| 2009/0230008 | A1 | 9/2009 | Miller et al. |
| 2010/0030159 | A1 | 2/2010 | Li |
| 2010/0041937 | A1 | 2/2010 | Gonzelez |
| 2010/0062921 | A1 | 3/2010 | Veiseh |
| 2010/0155400 | A1 | 6/2010 | Finnestad et al. |
| 2010/0234810 | A1 | 9/2010 | Arai et al. |
| 2010/0240818 | A1 | 9/2010 | Walton et al. |
| 2010/0268192 | A1 | 10/2010 | El-hibri et al. |
| 2010/0282623 | A1 | 11/2010 | Reshamwala |
| 2010/0331465 | A1 | 12/2010 | Zhao |
| 2011/0049763 | A1 | 3/2011 | Hackl |
| 2011/0068036 | A1 | 3/2011 | Ji et al. |
| 2011/0071230 | A1 | 3/2011 | Ji |
| 2011/0184082 | A1 | 7/2011 | Wright et al. |
| 2012/0245238 | A1 | 9/2012 | Zerafati et al. |

FOREIGN PATENT DOCUMENTS

| | | |
|---|---|---|
| JP | 2002-059082 | 2/2002 |
| JP | 2003-521396 | 7/2003 |
| JP | 2009-286106 | 12/2009 |
| JP | 2010504233 A | 2/2010 |
| WO | WO-91/01396 | 2/1991 |
| WO | WO-00/54885 | 9/2000 |
| WO | WO-01/34230 | 5/2001 |
| WO | WO-03/064522 | 8/2003 |
| WO | WO-2006/097105 | 9/2006 |
| WO | 2007024957 A1 | 3/2007 |
| WO | WO-2008/018920 | 2/2008 |
| WO | WO-2008/018921 | 2/2008 |
| WO | WO-2008/039438 | 4/2008 |
| WO | WO-2008/106759 | 9/2008 |
| WO | 2009100473 A1 | 9/2009 |
| WO | WO-2011/035119 | 3/2011 |

OTHER PUBLICATIONS

Meran, Cemal, et al., Examination of the possibility of recycling and utilizing recycled polyethylene and polypropylene, *Materials and Design 29* 2008, 701-705.

Weaver, Laura B., et al., Improving the Mechanical Properties of Polyethylene and Polypropylene Recycled Streams Using Polyolefin Elastomers and Functionalized Polyolefins, *The Dow Chemical Company* Jan. 25, 2001, 15 pages.

Zhao, Ruixiang, et al., Emerging Biodegradable Materials: starch- and protein-based bio-nanocomposites, *J Mater Sci* (2008) 43:3058-3071 Mar. 15, 2008, 14 pages.

Final Office Action in U.S. Appl. No. 12/859,972, dated Feb. 22, 2012, 14 pages.

Final Office Action in U.S. Appl. No. 12/859,972, dated May 9, 2013, 10 pages.

Final Office Action in U.S. Appl. No. 12/859,972, dated May 8, 2014, 10 pages.

Final Office Action in U.S. Appl. No. 12/859,972, dated Nov. 14, 2014, 10 pages.

Non-Final Office Action in U.S. Appl. No. 12/859,972, dated Nov. 3, 2011, 14 pages.

Non-Final Office Action in U.S. Appl. No. 12/859,972, dated Jan. 24, 2013, 9 pages.

Non-Final Office Action in U.S. Appl. No. 12/859,972, dated Jan. 24, 2014, 12 pages.

Non-Final Office Action in U.S. Appl. No. 12/859,972, dated Aug. 6, 2014, 12 pages.

PCT International Search Report in PCT/US2011/048103, mailed Sep. 29, 2011, 3 pages.

(56) References Cited

OTHER PUBLICATIONS

PCT International Written Opinion in PCT/US2011/048103, mailed Sep. 29, 2011, 6 pages.
PCT International Preliminary Report on Patentability in PCT/US2011/048103, dated Feb. 26, 2013, 7 pages.

* cited by examiner

RECYCLED RESIN COMPOSITIONS AND DISPOSABLE MEDICAL DEVICES MADE THEREFROM

CROSS-REFERENCE TO RELATED APPLICATIONS

This application is a continuation of U.S. patent application Ser. No. 12/859,972, now abandoned, filed on Aug. 20, 2010, the disclosures of which are incorporated herein by reference in their entirety.

TECHNICAL FIELD

The present invention relates to recycled resin compositions, medical devices formed from recycled resin compositions and methods for manufacturing medical devices from recycled resin compositions.

BACKGROUND

Plastics form a significant component of majority of disposable medical devices, non-disposable medical devices, medical device packaging as well as other non-medical device applications including automotive and commodity applications. These thermoplastics include polymers such as polypropylene, polyethylene, polystyrene, polyethyleneterephthalate and polycarbonate among others. Increasing use of plastics over the past decades has resulted in increased impact on landfill capacity and the depletion of fossil fuel-based resources. The increasing use of plastics or plastic material has also resulted in increasing level of environmental pollution and associated carbon footprint.

In light of above, there has been an increased interest in the utilization of recycled thermoplastic polymeric materials, which may be obtained from a variety of sources. The increased interest in utilizing recycled thermoplastic polymeric materials is driven by a number of factors, including increased customer awareness and concern for protection of the environment, environmentally preferred purchasing policies developed by customers, recognition of benefits of environmental stewardship in marketing by brand owners, development of new regulations and environmental policies intended to reduce the carbon footprint, and a desire to reduce the increasing costs of storage and/or landfill space coupled with more stringent regulations for disposal and incineration. The increased interest in utilizing recycled thermoplastic polymeric materials is also driven by the improved capabilities of recyclers to consistently produce high quality recycled resins. These factors have already resulted in extensive use of recycled plastics in automotive and food packaging applications. For example, Ford Motor Company has developed ways to increase the use of recycled materials in its vehicle manufacturing. Two exemplary outcomes of this development include Visteon Automotive Systems' recycling of thermoplastic scrap from automobile bumpers and E. I. du Pont de Nemours and Company recycling of scrap into automobile air cleaners. Recycled PET or polyethylene terephthalate is extensively used in food and packaging applications including beverage bottles.

In order to enhance the environmental stewardship of medical devices and ability of healthcare agencies to satisfy environmental targets, for example, the LEED system while reducing the impact on landfills, without sacrificing safety, there is a growing emphasis on manufacturing medical devices made from recycled plastics. Previous attempts to use recycled resins in manufacturing of medical devices or their components have encountered obstacles such as lack of biocompatibility, lot-to-lot variability in properties, and undesirable changes to the appearance during the sterilization process. Furthermore, when recycled resin compositions are used to form fluid path contact medical devices, there is a concern that the recycled resin compositions will interfere with the material being transmitted, carried or delivered through the medical device.

Accordingly, there is a need in the industry for thermoplastic compositions comprised of recycled resin compositions that are biocompatible, sterilization-stable and are useful for medical device applications. Such recycled resin compositions are not limited to medical device applications and would apply to any industry that may utilize such compositions that are sterilization-stable.

SUMMARY

A first aspect of the present invention pertains to a medical device. In one or more embodiments, the medical device is formed from a sterilization-stable recycled resin composition. In a more specific embodiment, the medical device is capable of withstanding sterilization that includes exposure to gamma rays in the range from about 5 kGys to about 75 kGys. The medical device may be capable of withstanding sterilization that includes exposure to an electron beam in the range from about 40 kGys to about 100 kGys or exposure to X-ray radiation, exposure to ethylene oxide gas, autoclaving, plasma sterilization and other types of sterilization. At least a portion of the medical device of one or more embodiments may include a fluid-path contact medical device or medical device that is in contact with fluid.

In one or more embodiments, the recycled resin composition is biocompatible, as defined above. The composition may include recycled resin that may be present in an amount in the range from about 0.1% to about 100% by weight. The recycled resin may include one of post-industrial recycled resin, post-consumer recycled resin and combinations thereof. In one or more embodiments, the recycled resin composition may include one or more of a virgin resin component and/or a biobased resin component.

The recycled resin composition may also include one or more of an antioxidant component, slip additive component, anti-static component, impact modifier component, colorant component, acid scavenger component, x-ray fluorescence agent component, radio opaque filler component, surface modifier component, processing aid component, melt stabilizer, clarifiers and reinforcing agent component. The antioxidant component may include one or more of hindered phenols and hindered amines and may optionally be present in an amount in up to about 10% by weight of the recycled resin composition. The impact modifier component utilized in one or more embodiments may include one or more of ethylene-butene copolymer and ethylene octane copolymer. The acid scavenger component may include one or more of calcium stearate, dihydro talcite, calcium lactate and monopotassium citrate. The radio opaque filler may include one or more of barium sulfate, bismuth subcarbonate, bismuth trioxide, bismuth oxychloride and tungsten, while the colorant component may include organic dyes, inorganic pigments, carbon black, channel black and titanium dioxide. The processing aid component utilized in one or more embodiments may include one or more of a fatty acid ester, fatty acid amide, wax and oxidized polyethylene. The reinforcing agent component may include one or more of glass fibers, cinderash, natural fibers and minerals, carbon fibers, ceramic fillers, which may be provided as nanoparticles or nanofibers.

The medical device of one or more embodiments may include a plunger rod, needle shield, handle, safety shield. In embodiments in which the medical device is a plunger rod, it exhibits functional performance that is acceptable to users including clinicians. In other words, the plunger rod may exhibit functional performance that is the same or greater than the functional performance exhibited by plunger rods formed from a non-recycled resin composition. The medical devices described herein may be formed by molding or extruding.

A second aspect of the present invention pertains to a composition for molding a medical device. The composition includes a recycled resin sourced from a traceable source and may optionally include one or more of an antioxidant component, slip additive component, anti-static component, impact modifier component, colorant component, acid scavenger component, x-ray fluorescence agent component, radio opaque filler component, surface modifier component, processing aid component, melt stabilizer component, clarifier component, nucleating agents and reinforcing agent component, as otherwise described above. In one or more embodiments, the composition is capable of withstanding exposure to gamma rays in the range from about 5 kGys to about 75 kGys. In another variant, the composition is capable of withstanding exposure to electron beams in the range from about 30 kGys to about 100 kGys. The composition may also optionally be capable of withstanding exposure to one of X-ray radiation, ethylene oxide gas, autoclaving and plasma sterilization.

The composition may be utilized to form the medical devices described herein. The composition may include one or more of a virgin resin component and a biobased resin component.

A third aspect of the present invention pertains to a method of forming a medical device. In one or more embodiments, the method includes providing a melt blend composition including a 50% to 99% recycled resin component, stabilizing the composition to withstand exposure to gamma rays, electron beams, X-ray radiations, ethylene oxide gas, autoclave, plasma sterilization and solidifying the composition in a pre-selected shape. In one or more embodiments, the method includes stabilizing the composition to withstand exposure to gamma rays in the range from about 5 kGys to about 75 kGys.

In one or more embodiments, the step of providing a melt blend composition includes feeding a recycled resin component and one or more of an antioxidant component, slip additive component, anti-static component, impact modifier component, colorant component, acid scavenger component, nucleating agents, clarifiers, x-ray fluorescence agent component, radio opaque filler component, surface modifier component, processing aid component and reinforcing agent component into a melt compounding extruder. The step of solidifying the composition may include injection molding the composition, extruding the composition, blow molding the composition and rotational molding the composition.

In one or more embodiments, the composition may be solidified in a pre-selected shape that includes one of a plunger rod, a syringe barrel, a catheter, a blood collection device, a surgical blade handle, a needle shield, safety shield, catheter wings, catheter flow control plugs and a needle hub, sharps containers, body fluid collection devices, tubing, adapters and drainage tubes.

DETAILED DESCRIPTION

Figure 1:
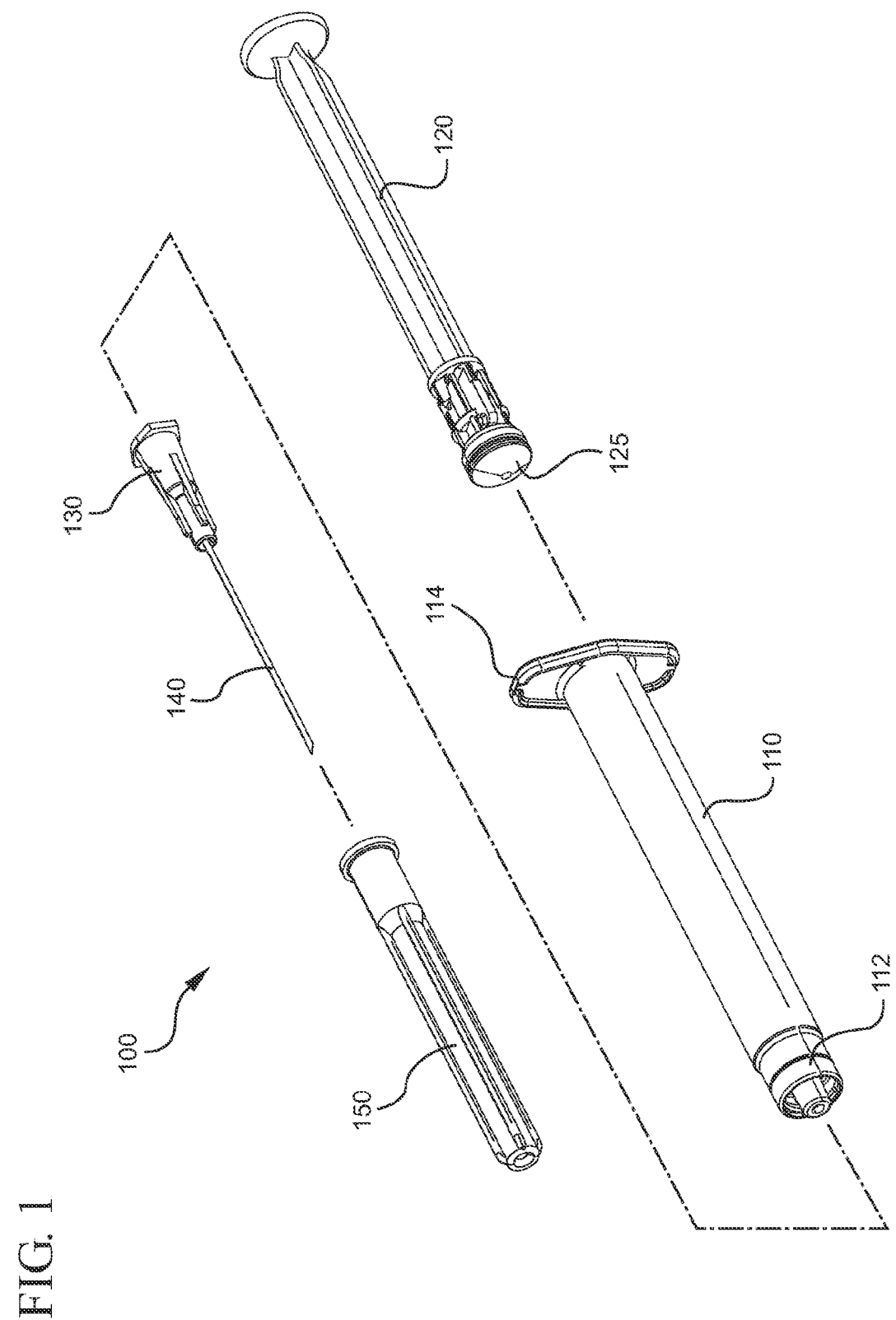
FIG. 1 illustrates an exploded view of a syringe assembly of one or more embodiments of the present invention.

Before describing several exemplary embodiments of the invention, it is to be understood that the invention is not limited to the details of construction or process steps set forth in the following description. The invention is capable of other embodiments and of being practiced or being carried out in various ways.

As used herein, the term "medical device" shall include all devices and components used in conjunction with other components in devices that are used in all medical and/or laboratory purposes, excluding waste collection containers such as sharps collection containers. Medical devices include syringe assemblies, including syringe barrels, plunger rods, catheters, needle hubs and needle shields, safety shields, surgical blades, surgical handles, sharps containers, body fluid collection devices, tubing, adapters, shunts, drainage tubes, guidewires, stents, petri dishes, culture bottles, centrifuge tubes, blood collection devices and the like. As indicated, as used herein "medical devices" excludes waste collection containers such as sharps collection containers.

As used herein, the term "biocompatible" shall mean any substance that is not toxic to the body or biological environment or does not produce an undesirable biological response during the period of exposure to the human body. A composition is biocompatible if the composition, and any degradation products of the composition, are non-toxic to the recipient or biological environment and also present no significant deleterious effects on the biological environment. A medical device is biocompatible if the medical device, and any degradation products of the medical device, are non-toxic to the recipient or biological environment and also present no significant deleterious effects on the biological environment.

In addition, as used herein, the term "sterilization-stable" shall mean the ability of a medical device or component to withstand sterilization without significant loss of functional performance and mechanical properties. Sterilization includes exposure to radiation, for example, gamma rays and/or X-rays, during the sterilization process. Medical devices or components thereof that are capable of withstanding radiation sterilization without significant loss of functional performance may be referred to as "radiation stable." An example of a sterilization process may include exposure of a medical device to high energy photons that are emitted from an isotope source, for example Cobalt 60, which produces ionization or electron disruptions throughout the medical device. Sterilization may also include ethylene oxide sterilization, electron bean sterilization, autoclave (steam sterilization), plasma sterilization, dry heat sterilization, and X-ray beam sterilization.

As used herein, "fluid path contact medical devices" are medical devices wherein at least a portion of the medical device comes into contact or interacts with fluids and/or solids, for example, medications, solutions of medications, drug containing solutions, flush solutions, body fluids, human tissue, or any material that is intended to be isolated to prevent contamination. As used herein, reference to a medical device "formed from a sterilization-stable recycled resin composition" means that the device is manufactured, for example, shaped from a resin obtained from recycled resin. Accordingly, a medical device "formed from a sterilization-stable recycled resin composition" does not include a medical device that is used, and then reprocessed by cleaning or sterilization of a part of or the entire device by radiation or in an autoclave. Such reuse of medical device is often referred to as "reprocessing", and reprocessed medical devices are not within the scope of a device formed from a sterilization-stable recycled resin composition because such reprocessing does not include shaping or other manufacturing process to form a device from a resin composition A first aspect of the present invention pertains to compositions for use in molding a medical device that includes a recycled resin from a traceable source. A second aspect of the present invention pertains to a medical device that is formed from a recycled resin composition. A third aspect of the present invention pertains to a method of forming a medical device.

The recycled resin compositions of one or more embodiments of the first aspect may include a post-industrial recycled resin. The amount of post-industrial recycled resin may be present in the recycled resin composition in the range from about 0.1% to about 100% by weight of the recycled resin composition. In one or more embodiments, the recycled resin composition includes post-industrial recycled resin in an amount in the range from about 50% to about 99% by weight. In one or more specific embodiments, the recycled resin composition may include post-industrial recycled resin in an amount in the range from about 20% to about 80% by weight. In a more specific embodiment, the lower limit of the amount of post-industrial recycled resin may include 25%, 30%, 35%, 40%, 45% and 50% by weight of the recycled resin composition and all ranges and sub-ranges therebetween. The upper limit of the amount of post-industrial recycled resin may include 75%, 70%, 65%, 60%, 55% and 50% by weight of the recycled resin composition and all ranges and sub-ranges therebetween.

The recycled resin compositions of one or more embodiments of the first aspect may include a post-consumer recycled resin. The resin may be provided in any suitable form, such as in the form of flakes, chips, pellets and the like. In one variant, the recycled resin compositions may include post-consumer recycled resin and post-industrial recycled resin. The amount of post-consumer recycled resin may be present in the recycled resin composition in the range from about 0.1% to about 100% by weight of the recycled resin composition. In one or more embodiments, the recycled resin composition includes post-consumer recycled resin in an amount in the range from about 50% to about 99% by weight. In one or more specific embodiments, the recycled resin composition may include post-consumer recycled resin in an amount in the range from about 20% to about 80% by weight. In a more specific embodiment, the lower limit of the amount of post-consumer recycled resin may include 25%, 30%, 35%, 40%, 45% and 50% by weight of the recycled resin composition and all ranges and sub-ranges therebetween. The upper limit of the amount of post-consumer recycled resin may include 75%, 70%, 65%, 60%, 55% and 50% by weight of the recycled resin composition and all ranges and sub-ranges therebetween.

Examples of suitable post-industrial recycled resins and post-consumer recycled resins include polypropylene, polycarbonates, nylons, polyethyleneterphthalates, polyesters, polyethylenes, polystyrenes, poly lactic acid, polyhyroxyalkanoates, bioderived polyolefins including polyethylene and polypropylene and other resins known in the art that are recyclable and combinations thereof. The recycled resins may have been recovered or otherwise diverted from the solid waste stream, either during the manufacturing process (pre-consumer), or after consumer use (post-consumer).

In one or more embodiments, the recycled resin composition may also include one or more of the optional additives. These optional additives are selected from the group consisting of anti-oxidants, slip additives, anti-static agents, impact modifiers, a colorants, acid scavengers, X-ray fluorescence agents, radio opaque fillers, surface modifiers, processing aids including melt stabilizers, nucleating agents including clarifiers, flame retardants, inorganic fillers other than finely powdered talc, organic fillers and other polymers and reinforcing agents.

In one or more embodiments, the recycled resin composition includes an anti-oxidant component. The anti-oxidant component may include chemical compounds that inhibit oxidation via chain terminating reactions. In one or more embodiments, the anti-oxidant component may be present in the recycled resin composition in an amount up to about 10% by weight of the recycled resin composition. In one or more specific embodiments, the recycled resin composition may include an anti-oxidant component in an amount of up to about 5% by weight or, more specifically, an amount of up to about 1% by weight of the recycled resin composition. In one or more specific embodiments, the anti-oxidant component may be present in an amount in the range from about 1% by weight to about 5% by weight of the recycled resin composition. In an even more specific embodiment, the anti-oxidant component may be present in an amount in the range from about 0.1% to about 1% by weight of the recycled resin composition. The upper limit of the amount of the anti-oxidant component may include 0.9%, 0.8%, 0.7%, 0.6% and 0.5% and all ranges and sub-ranges therebetween.

In one or more embodiments, the anti-oxidant component is present in an amount sufficient to inhibit oxidation reactions during sterilization and over the shelf life and/or use-phase of the product.

Non-exclusive examples of suitable anti-oxidant components include hindered phenols, hindered amines, phosphites and/or combinations thereof. Hindered phenols include chemical compounds that act as hydrogen donors and react with peroxy radicals to form hydroperoxides and prevent the abstraction of hydrogen from the polymer backbone. Suitable hindered phenols include buylated hydroxytoluene. Other suitable hindered phenols are available under the trademark Irganox® 1076, Irganox® 1010, and Irganox®E 201, from Ciba, Inc., now part of BASF Corporation of Ludwigshafen, Germany. Other examples of hindered phenols include BNX®1010 and BNX®1076TF from Mayzo Inc. or Norcross, Ga., U.S.A. Suitable hindered phenols are also available under the trademark Ethanox®330 and Ethanox®376 from Albemarle Corporation of Baton Rouge, La., U.S.A.

Hindered amines include chemical compounds containing an amine functional group surrounded by a steric environment. They are extremely efficient stabilizers against light-induced degradation of most polymers. Examples of suitable hindered amines include bis(1,2,2,6,6-pentamethyl-4-piperidinyl)-2-n-butyl-2-(3,5-di-tert-butyl-4-hydroxybenzyl)malonate; bis(2,2,6,6-tetramethyl-4-piperidinyl)sebacate, bis (1,2,3,6,6-pentamethyl-4-piperidinyl)sebacate and bis(1,2,2, 6,6-pentamethyl-4-piperidinyl)sebacate. These are commonly referred to as Tinuvin 144, Tinuvin 770, Tinuvin 292 and Tinuvin 765 respectively and are available from the Ciba-Geigy Corporation, now part of BASF Corporation of Ludwigshafen, Germany. Other examples of suitable hindered amines are available under the tradenames Uvasorb HA-88 from 3V Sigma SpA of Bergamo, Italy, and Chimassorb 944 and Chimassorb 994 from BASF Corporation of Ludwigshafen, Germany.

In specific embodiments, the recycled resin composition includes a slip additive component. The slip additive component may include chemical compounds reduce the surface coefficient of friction of polymers and are used to enhance either processing or end applications. The slip additive component may be present in the recycled resin composition in an amount in the range from about 0.001% to about 5% by weight of the recycled resin composition and all ranges and sub-ranges therebetween. In one or more specific embodiments, the slip additive component is present in an amount in the range from about 1% to about 2% by weight of the recycled resin composition. The upper limit of the amount of the slip additive component may include 4.5%, 4.0%, 3.5%, 3.0%, and 2.5% by weight of the recycled resin composition and all ranges and sub-ranges therebetween. The lower limit of the amount of the slip additive component may include 0.1%, 0.2%, 0.3%, 0.4%, 0.5%, 0.6%, 0.7%, 0.8%, and 0.9% by weight of the recycled resin composition and all ranges and sub-ranges therebetween. Examples of suitable slip additive components include oleamides, erucamide, Oleyl palmitamide, Stearyl erucamide, Ethylene-bis-oleamide, waxes and combinations thereof.

The recycled resin composition optionally includes an anti-static component. The anti-static component may include chemical compounds that prevent or reduce the accumulation of static electricity. The anti-static component acts to permit the body or surface of the material to be static dissipative, preventing the formation of static charges and hindering the fixation of dust. The anti-static component may be incorporated in the material before molding, or applied to the surface after molding and function either by being inherently static dissipative or by absorbing moisture from the air. The anti-static component may be present in the recycled resin composition in an amount in the range from about 0.01% to about 5% by weight of the recycled resin composition and all ranges and sub-ranges therebetween. In one or more specific embodiments, the anti-static component is present in an amount in the range form about 0.1% to about 3.0% by weight of the recycled resin composition and all ranges and sub-ranges therebetween. The upper limit of the amount of the anti-static component may include 4.5%, 4.0%, 3.5%, 3.0% and 2.5% by weight of the recycled resin composition and all ranges and sub-ranges therebetween. The lower limit of the amount of the anti-static component may include 0.1%, 0.2%, 0.3%, 0.4%, 0.5%, 0.6%, 0.7%, 0.8%, 0.9% and 1.0% by weight of the recycled resin composition and all ranges and sub-ranges therebetween. Examples of anti-static agent components are long-chain aliphatic amines and amides, phosphate esters, quaternary ammonium salts, polyethylene glycols, polyethylene glycol esters, ethoxylated long-chained aliphatic amines and combinations thereof. Other examples of suitable anti-static agents are available under the trade name Pelestat 230 and Pelestat 300 from Toyota Tsusho Corporation of Nagoya, Japan, Atmer™ 163 from Uniqema, now part of Croda International Plc of Yorkshire, England, U.K, Entira™MK 400 from E.I DuPont de Nemours and Company of Wilmington, Del., U.S.A and Nourymix® AP 375 and 775 from Akzo Nobel N.V. of Amsterdam, the Netherlands.

The recycled resin composition optionally includes an impact modifier component. The impact modifier component may include chemical compounds for improving the impact resistance of finished articles or devices. The impact modifier component may be present in the recycled resin composition in an amount in the range from about 0.1% to about 30% by weight of the recycled resin composition. In one or more specific embodiments, the impact modifier component is present in an amount in the range form about 0.5% to about 5% by weight of the recycled resin composition and all ranges and sub-ranges therebetween. The upper limit of the amount of impact modifier component may include 4.5%, 4.0%, 3.5%, 3.0%, 2.5% and 2.0% by weight of the recycled resin composition and all ranges and sub-ranges therebetween. The lower limit of the amount of impact modifier component may include 0.75%, 1.0%, 1.25%, 1.5%, 1.75% and 2.0% by weight of the recycled resin composition and all ranges and sub-ranges therebetween. Examples of suitable impact modifier components include ethylene-butene copolymers, ethylene octene copolymers, ethylene-propylene copolymers, methacrylate butadiene-styrene core shell impact modifiers and combinations thereof. Examples of suitable impact modifier agents are available under the trade name Elvaloy® EAC3427 from E.I DuPont de Nemours and Company of Wilmington, Del., U.S.A., Engage™ and Versify™ from the Dow Chemical Company of Midland, Mich., U.S.A. and Clearstrength™ from Arkema Inc. of Philadelphia, Pa., U.S.A.

When present, the impact modifier component can be present in an amount sufficient to meet the impact requirements of the fabricated medical article.

The recycled resin composition optionally includes an acid scavenger component. The acid scavenger component may include chemical compounds for preventing discoloration or premature aging of the polymer as well as the fabricated medical article from the acidic impurities during the course of manufacturing, processing, sterilization, shelf life or use phase. For example, such chemical compounds may neutralize halogen anions found in resin compositions that may be formed due to the influence of heat and shear during processing. The acid scavenger component scavenges these halogenic acids to prevent polymer degradation or corrosion. The acid scavenger component may be present in the recycled resin composition in an amount in the range from about 0.01% to about 1% by weight of the recycled resin composition. In one or more specific embodiments, the acid scavenger component is present in an amount in the range form about 0.1% to about 0.5% by weight of the recycled resin composition and all ranges and sub-ranges therebetween. The upper limit of the amount of acid scavenger component may include 0.6%, 0.7%, 0.8%, and 0.9% by weight of the recycled resin composition and all ranges and sub-ranges therebetween. The lower limit of the amount of acid scavenger component may include 0.01%, 0.02%, 0.03%, 0.04%. 0.05%, 0.06%. 0.07%, 0.08% and 0.09% by weight of the recycled resin composition and all ranges and sub-ranges therebetween. Examples of suitable acid scavenger components include metal salts of long chain carboxylic acids like calcium, zinc or sodium stearates, lactates, natural or synthetic silicates like hydrotalcites, metal oxides (e.g. magnesium oxide, calcium oxide, zinc oxide), metal carbonates (e.g. calcium carbonate) or metal hydroxides (see e.g. A Holzner, K Chmil in H. Zweifel, Plastic Additives Handbook, 5$^{th}$ Ed., Hanser Publisher, Munich 2001, Chapter 4 Acid Scavengers). Suitable examples of acid scavengers include calcium stearate, dihydro talcite, calcium lactate, mono potassium citrate and combinations thereof.

When present, the acid scavenger component can be present in the recycled resin composition in an amount sufficient to inhibit discoloration and prevent degradation caused by acidic impurities during manufacturing, processing, storage, shelf life or use phase of polymer and medical article fabricated therefrom.

Another optional component of the recycled resin composition is a radio opaque filler component. The radio opaque filler component may include chemical compounds for that cause medical devices formed from the resin composition to be visible under fluoroscopy or x-ray imaging. The radio opaque filler component may be present in the recycled resin composition in an amount in the range from about 10% to about 48% by weight of the recycled resin composition and all ranges and sub-ranges therebetween. In one or more specific embodiments, the radio opaque filler component is present in an amount in the range from about 22% to about 25% by weight of the recycled resin composition and all ranges and sub-ranges therebetween. The upper limit of the amount of the radio opaque filler component may include 26%, 28%, 30%, 32%, 34%, 36%, 38%, 40%, 42%, 44% and 46% by weight of the recycled resin composition and all ranges and subranges therebetween. The lower limit of the amount of the radio opaque filler component may include 11%, 12%, 13%, 14%, 15%, 16%, 17%, 18%, 19% and 20% by weight of the recycled resin composition and all ranges and subranges therebetween. Higher percentages of radio opaque filler component may also be used. For example, the amount of the radio opaque filler component may be more than about 50% by weight of the recycled resin composition. Examples of suitable radio opaque filler components include barium sulfate, bismuth subcarbonate, bismuth trioxide, bismuth oxychloride, tungsten and combinations thereof.

The radio opaque filler component can be present in an amount sufficient to enable visibility of the medical devices using x-ray and other radiology imaging techniques.

The recycled resin composition further optionally includes a surface modifier component. The surface modifier component may include chemical compounds or materials which tailor the surface of the fabricated component(s) to meet or enhance adhesion, lubricity and/or physical properties. The surface modifier component may be present in the recycled resin composition in an amount in the range from about 0.1% to about 10% by weight of the recycled resin composition. In one or more specific embodiments, the surface modifier component is present in an amount in the range form about 0.5% to about 5%, more preferably between 0.2 to 1% by weight of the recycled resin composition and all ranges and sub-ranges therebetween. The upper limit of the amount of the surface modifier component may include 1.5%, 2.0%, 3.0%, 3.5%, 4.0% and 4.5% and all ranges and sub-ranges therebetween. The lower limit of the amount of the surface modifier component may include 0.3%, 0.35%, 0.4% and 0.45% by weight of the recycled resin composition and all ranges and sub-ranges therebetween. In one or more embodiments, higher percentages of surface modifiers may also be used. Examples of suitable surface modifier components include diatomaceous earth, talc, calcium carbonate, organosilanes, titanates, maleated polyolefins, powdered PTFE and combinations thereof.

The surface modifier can be present in the recycled resin composition in an amount sufficient to impart desirable surface property to the surface of the fabricated medical device.

In one or more embodiments, the recycled resin composition includes a colorant component. The colorant component may be present in the recycled resin composition in an amount in the range from about 0.01% to about 5% by weight of the recycled resin composition. In one or more specific embodiments, the colorant component(s) are present in an amount in the range form about 0.5% to about 3% by weight of the recycled resin composition and all ranges and sub-ranges therebetween. The upper limit of the amount of colorant component may include 3.25%, 3.5%, 3.75%, 4.0%, 4.25%, 4.5% and 4.75% by weight of the recycled resin composition and all ranges and sub-ranges therebetween. The lower limit of the amount of the colorant component may include 0.1%, 0.15%, 0.2%, 0.25%, 0.3%, 0.35%, 0.4% and 0.45% by weight of the recycled resin composition and all ranges and sub-ranges therebetween. Examples of suitable colorant components include organic dyes, inorganic pigments, carbon black, channel black, titanium dioxide and combinations thereof. Organic dyes may include Phthalocyanine blue and Phthalocyanine green, and FD&C colorants. Exemplary inorganic pigments include ultramarines and iron oxides.

Another optional component of the recycled resin composition includes a processing aid component. The processing aid component may include chemical compounds which improve the processability of high molecular weight polymers, reduces the cycle time and help improve quality of finished products. The processing aid component may be present in the recycled resin composition in an amount in the range from about 0.05% to about 5% by weight of the recycled resin composition and all ranges and sub-ranges therebetween. In one or more specific embodiments, the processing aid component is present in an amount in the range form about 0.1 to about 3% by weight of the recycled resin composition and all ranges and sub-ranges therebetween. The upper limit of the amount of colorant component may include 3.25%, 3.5%, 3.75%, 4.0%, 4.25%, 4.5% and 4.75% by weight of the recycled resin composition and all ranges and sub-ranges therebetween. The lower limit of the amount of the colorant component may include 0.06%, 0.07%, 0.08% and 0.09% by weight of the recycled resin composition and all ranges and sub-ranges therebetween. Higher percentages of processing aid may also be used. Examples of suitable processing aid components include fatty acid esters, fatty acid amines, waxes, oxidized polyethylenes, colloidal fumed silica particles and combinations thereof. Colloidal fumed silica particles are available under the tradename Nan-O-Sil ASD from Energy Strategy Associates, Inc. of Old Chatham, N.Y., USA. Glycerol monostearates and bisstearaamides are suitable fatty acid esters and fatty acid amides.

The recycled resin composition may optionally include a nucleating agents and/or clarifier component. Nucleating agents may include chemical compounds that enhance resin performance properties such as stiffness and heat resistance. A clarifier may also be added to enhance the aesthetic appeal of a formed product by making it more transparent. In one or more embodiments, the nucleating and/or clarifier component is present in an amount in the range from about 0.005% to about 3% by weight of the recycled resin composition. Higher percentages of nucleating and/or clarifying agents may be used but generally provide no perceived advantages. In one or more specific embodiments, the clarifier component is present in an amount in the range from about 0.05 to about 0.5% by weight of the recycled resin composition and all ranges and sub-ranges therebetween. The upper limit of the amount of the clarifier component may include 1.0%, 1.5%, 2.0% and 2.5% by weight of the recycled resin composition and all ranges and sub-ranges therebetween. The lower limit of the amount of the clarifier component may include 0.01%, 0.015%, 0.02%, 0.025%, 0.03%, 0.035%, 0.04% and 0.045% by weight of the recycled resin composition and all ranges and sub-ranges therebetween. Examples of clarifier components include dibenzylidene sorbitol as described in U.S. Pat. No. 4,016,118, which is incorporated herein by reference, substituted dibenzylidene sorbitol as described in U.S. Pat. No. 4,371,645, which is incorporated herein by reference, and dibenzylidene sorbitol thioether derivatives as described in U.S. Pat. No. 4,994,552, which is incorporated herein by reference.

When present, the clarifiers can be present in an amount sufficient such that the size of the size of the crystals in the resulting resin composition is smaller than the wavelength of visible light to prevent light scattering, which causes opacity.

The recycled resin composition optionally includes a reinforcing agent component. The reinforcing agent component may be present in the recycled resin composition in an amount in the range from about 1% to about 35% by weight of the recycled resin composition. In one or more specific embodiments, the reinforcing agent component(s) are present in an amount in the range from about 5% to about 30% by weight of the recycled resin composition and all ranges and sub-ranges therebetween. The upper limit of the amount of the reinforcing agent component may include 30.5%, 31%, 31.5%, 32%, 32.5%, 33%, 33.5%, 34% and 34.5% by weight of the recycled resin composition and all ranges and sub-ranges therebetween. The lower limit of the amount of the reinforcing agent component may include 1.5%, 2%, 2.5%, 3%, 3.5%, 4% and 4.5% by weight of the recycled resin composition and all ranges and sub-ranges therebetween. Examples of suitable reinforcing agent components include glass fibers, cinderash, natural fibers and minerals, carbon fibers, ceramic fibers, and combinations thereof. Examples of natural fibers include flax fibers and kenaf fibers and fillers. The reinforcing agent component may be present in the recycled resin composition in the form of nanofibers and/or nanoparticles.

The recycled resin composition according to one or more embodiments may optionally include a melt stabilizer component. The melt stabilizer component may include chemical compounds for adjusting the viscosity of the recycled resin composition during a melting process.

The recycled resin composition may also optionally incorporate a non-recycled resin component. Examples of a non-recycled resin component include virgin resin components, biobased resin components and combinations thereof. Virgin resin components are resin compositions that do not include a significant amount of recycled resin. In one or more embodiments, virgin resin components are free of recycled resin. Virgin resin components may also include "fossil fuel-based polymers" or "petroleum based polymers," which shall be used interchangeably, and include, without limitation, polymers formed from non-renewable sources such as fossil fuel sources. Such polymers include polypropylene, polyethylene not derived from sugar or other renewable resources, polycarbonate.

The term "biobased" may be used interchangeably with the terms "bioformed" and "bioderived." The biobased component includes polymers that are derived, produced or synthesized in whole or in significant part, from biological sources or renewable domestic agricultural materials (including plant, animal, and marine materials) or forestry materials. The biobased component includes polymers in which carbon is derived from a renewable resource via biological processes such as microbiological fermentation. The biobased component may also include polymers with cellulose-based materials of different grades. The biobased component may also include polymers are that substantially free of materials derived from fossil fuel or non-renewable resources as determined by ASTM D6866-08.

The biobased component used herein may include polymers which are derived from biological sources, such as plants, and include polysaccharide-derived polymers, such as starch- or carbohydrate-derived polymers, and sugar-derived polymers. The starch used to form bioformed polymers may be derived from corn, potatoes, wheat, cassava, rice and other plants. An example of a composition containing bioformed polymer derived from starch is available from Cereplast Inc., Hawthorne, Calif., U.S.A., under the trademarks and trade names Cereplast Hybrid Resins, Bio-polyolefins®, or Biopropylene 50™. The sugar used to form such bioformed polymers may be derived from sugar cane. Such sugar-derived polymers include polyethylene, which may be produced from ethanol derived from sugar cane, which is then used to produce ethylene and polymers are available from Novamount S.P.A., Novara, Italy under the trademark MATER-BI®. Other examples of bioformed polymers are described in U.S. Pat. No. 7,393,590, U.S. Patent Application Publication Nos. 2008/0113887 and 2008/0153940, PCT Application Publication Nos. WO07/099427 and WO07/063361 and European Patent No. 1725614, each of which is incorporated herein in their entirety by reference. A specific example of a bioformed polymer includes "poly(lactic acid)" or "PLA," which may include a synthetic polymer produced from cane sugar or cornstarch. PLA is available from NatureWorks LLC, Minnetonka, Minn., U.S.A., under the trade name Ingeo™. Embodiments utilizing PLA may also include an ethylene copolymer. Ethylene copolymers are available from E. I. du Pont de Nemours and Company, Wilmington, Del., U.S.A., under the trademark BIOMAX®.

Biobased component includes polymers may also be produced from microbes. Microorganisms produce substances, including polymers, by growth on feedstock, including sugar feedstock. The production of these polymers may also involve bacterial fermentation of sugar or lipids. The biobased component may be further treated or synthesized from natural products. Examples of such produced and/or synthesized biobased polymers include polyhydroxyalkanoates The term "polyhydroxyalkanoate" or "PHA" includes linear polyesters produced in nature by bacterial fermentation of sugar or lipids. Examples of PHAs include poly(hydroxybutyrate) and poly(hydroxyvalerate) or "PHBV." PHAs may exhibit properties such as elasticity. PHAs are available from Metabolix, Inc., Cambridge, Mass., U.S.A., under the trademark MIREL.

Recycled resin compositions according to one or more embodiments, are biocompatible, as defined herein. In one or more embodiments, the recycled resin composition is capable of withstanding exposure to gamma rays, electron beams, X-rays, ethylene oxide gas, dry heat, peroxide gas plasma, peracetic acid, steam autoclave and other means of sterilization. In one or more embodiments, the recycled resin composition is radiation stable and capable of withstanding exposure to gamma rays in the range from about 5 kGys to about 75 kGys, or more specifically, in the range from about 25 kGys to about 50 kGys. In one or more embodiments, the recycled resin composition is capable of withstanding exposure to electron beams in the range from about 30 kGys to about 80 kGys, or, more specifically, in the range from about 40 kGys to about 70 kGys.

The recycled resin composition according to one or more embodiments has a melt flow rate in the range from about 3 dg/minute to about 80 dg/minute. In one or more specific embodiments, the recycled resin composition has a melt flow rate in the range from about 8 dg/minute to about 40 dg/minute. In even more specific embodiments, the recycled resin composition has a melt flow rate in the range from about 11 dg/minute to about 30 dg/minute. As used herein, the term "melt flow rate" refers to the ease of flow of the melt of the recycled resin compositions described herein.

The recycled resin compositions described herein may have a flexural modulus in the range from about 70 kpsi to 350 kpsi and all ranges and subranges therebetween as measured according to ASTM D790 test method. In one or more specific embodiments, the recycled resin compositions have a flexural modulus in the range from about 100 kpsi to about 300 kpsi. In even more specific embodiments, the recycled resin compositions exhibits a flexural modulus in the range from about 130 kpsi to about 270 kpsi.

The recycled resin composition may be characterized by having notched izod impact strength in the range from about 0.1 ft-lb/in. to about 4.0 ft-lb/in and all ranges and subranges as measured according to ASTM D256 test method. In one or more embodiments, the recycled resin composition may have notched izod impact strength in the range from about 0.2 ft-lb/in. to about 1.5 ft-lb/in. In one or more specific embodiments, the recycled resin composition may have a notched izod impact strength in the range from about 0.3 ft-lb/in. to about 1.0 ft-lb/in. As used herein, the term "notched izod impact strength" refers to the ASTM standard method of determining impact strength.

One or more embodiments of the recycled resin composition described herein may be characterized by having a heat deflection temperature in the range from about 60° C. to about 260° C. As used herein, the term "heat deflection temperature" includes a measure of a polymer's resistance to distortion under a given load at elevated temperature. The heat deflection temperature is also known as the 'deflection temperature under load' (DTUL), deflection temperature, or 'heat distortion temperature' (HDT). The two common loads used to determine heat deflection temperature are 0.46 MPa (66 psi) and 1.8 MPa (264 psi), although tests performed at higher loads such as 5.0 MPa (725 psi) or 8.0 MPa (1160 psi) are occasionally encountered. The common ASTM test is ASTM D 648 while the analogous ISO test is ISO 75. The test using a 1.8 MPa load is performed under ISO 75 Method A while the test using a 0.46 MPa load is performed under ISO 75 Method B. In one or more specific embodiments, the recycled resin composition may have a heat deflection temperature in the range from about 68° C. to about 140° C. In even more specific embodiments, the recycled resin composition may have a heat deflection temperature in the range from about 70° C. to about 95° C. In one or more embodiments which utilize a post-industrial recycled resin component comprising polycarbonate, the recycled resin composition has a heat deflection temperature of about 140° C. at a load of 0.46 MPa and 130° C. at a load of 1.8 MPa. In one or more embodiments which utilize a post-industrial recycled resin component comprising nylon and a reinforcing agent component including glass fibers, the recycled resin composition has a heat deflection temperature of about 220° C. at a load of 0.46 MPa and 200° C. at a load of 1.8 MPa. In embodiments which utilize a post-industrial recycled resin component comprising PET and a reinforcing agent component including glass fibers, the recycled resin composition has a heat deflection temperature of about 250° C. at a load of 0.46 MPa and 230° C. at a load of 1.8 MPa.

Preparation of the recycled resin compositions of this invention can be accomplished by any suitable blending or mixing means known in the art. The blending step should, at least minimally, disperse the components amongst each other. The components may be blended together in a one-step process or a multi-step process. In the one-step process, all the components are blended together at the same time. In the multiple-step process, two or more components are blended together to form a first mixture and then one or more of the remaining components are blended with the first mixture. If one or more components still remain, these components may be blended in subsequent mixing steps. In one or more embodiments, all the components are blended in a single step.

In one or more alternative embodiments, the recycled polypropylene composition may be prepared by dry blending the individual components and subsequently melt mixing, either directly in the extruder used to make the finished article, or premixing in a separate extruder. Dry blends of the composition may also be directly injection molded without pre-melt mixing.

The recycled resin compositions disclosed herein are utilized to mold, extrude or otherwise form a medical device. In one or more embodiments, the medical device is disposable. For example, the medical devices may be formed from the recycled resin compositions described herein may be used in injection, infusion, blood collection, surgical applications and other applications known in the art. Specific examples of medical devices that may be formed form the recycled resin compositions described herein include syringes (including syringe barrels, needle hub parts, plunger rods, needle shields and the like), safety syringes, catheters, blood collection devices, surgical blades or scalpels and other such devices and components. In one or more alternative embodiments, the medical device may be entirely or partially molded from a recycled resin composition. For example, the inside surface of a syringe barrel may be formed from a resin composition that is not recycled while the outside surface of the syringe barrel or the finger flanges of the syringe barrel are made from a recycled resin composition. In one or more alternative embodiments, the scalpel handle or needle shield are formed from a recycled resin composition.

In one or more embodiments, the medical devices formed from the recycled resin compositions described herein may be characterized as non-fluid path contact components or medical devices. As such, the medical devices and components do not interact or come into contact with fluids and/or solids, for example, medications, solutions of medications, drug containing solutions, flush solutions, body fluids, human tissue, or any material that is intended to be isolated to prevent contamination. Examples of such devices include syringe plunger rods of a three-piece syringe, needle shields, safety shields of injection devices and the finger flanges of a syringe barrel, handle of peripheral IV catheter, catheter wings, catheter flow control plug etc. Medical devices and components formed from recycled resin compositions may also be characterized as fluid path contact medical devices. Such medical devices or medical device components may include syringe barrels, needle hubs, surgical blade handles, valve housings, syringe stopper, plunger rod of a two piece syringe.

Figure 2:
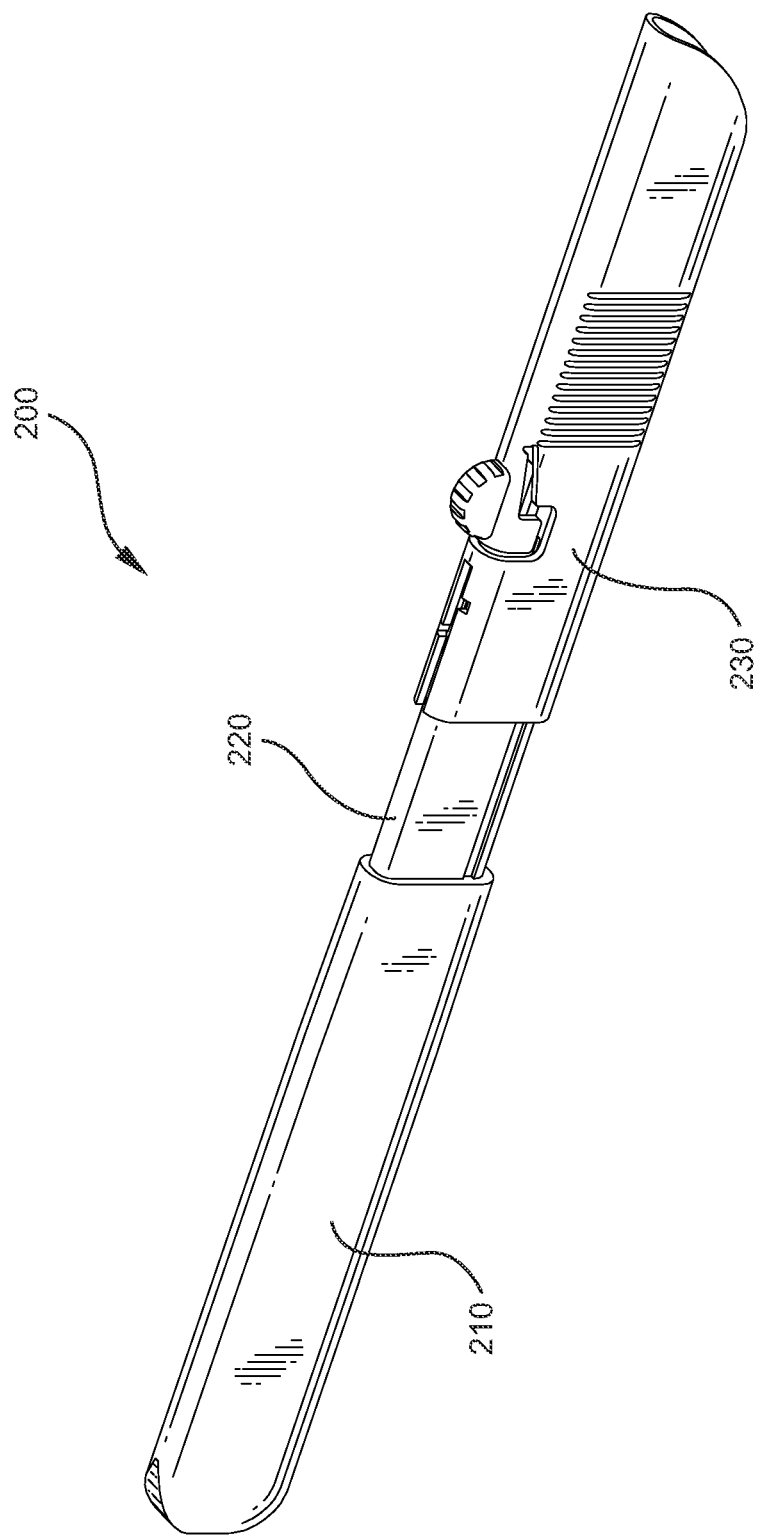
FIG. 2 illustrates a perspective view of a scalpel and scalpel shield according to one or more embodiments.

Non-limiting examples of medical devices are illustrated in FIGS. 1 and 2. FIG. 1 illustrates a syringe assembly 100 including a syringe barrel 110 with an inside surface defining a chamber, a plunger rod 120 disposed within the chamber, a needle hub 130 including a needle cannula 140 for attachment to the syringe barrel. FIG. 1 also illustrates an optional needle shield 150 to be attached to the needle hub 130 to protect and cover the needle cannula 140. The plunger rod 120 may include a separate stopper 125 attached to one end of the plunger rod 120 for forming a fluid tight seal with the inside surface of the syringe barrel, as shown in FIG. 1. In one or more alternative embodiments, the plunger rod 120 may include a sealing portion (not shown) that functions as a stopper, and may be integrally molded with the plunger rod 120 and thus formed form the same material as the plunger rod 120. The syringe barrel 110 shown in FIG. 1 also includes a luer fitting 112 at one end of the syringe barrel 110 and a finger flange 114 at the opposite end of the syringe barrel 110.

In one variant, the syringe barrel may be entirely formed from the recycled resin compositions disclosed herein. Alternatively, the luer fitting 112 and/or the finger flanges 114 may be formed from the recycled resin compositions disclosed herein, while the syringe barrel 110 is formed from known resin compositions that may include virgin resin components and/or biobased resin components, and are free of any recycled resin. In one or more alternative configurations, the inside surface of the syringe barrel 110 may be coated with known a resin composition(s) that may include virgin resin components and/or biobased resin components, and are free of any recycled resin, while the remainder of the syringe barrel 110 is formed form one or more of the recycled resin compositions described herein.

In one variant, the plunger rod 120 may be formed from the recycled resin compositions described herein. In embodiments which incorporate a sealing edge (not shown) into the plunger rod 120, the sealing edge (not shown) may also be formed from the recycled resin compositions described herein. In one or more embodiments, the stopper 125 may be formed from elastomeric or other known materials, while the plunger rod is formed from the recycled resin compositions and is attached to the stopper 125.

In one or more embodiments, the needle hub 130 may be formed from the recycled resin compositions described herein, while the needle cannula 140 is made from known materials in the art. In one or more alternative configurations, the needle shield 150 may also be formed from the recycled resin compositions disclosed herein.

FIG. 2 illustrates a scalpel 200 that includes an elongate handle 210 and blade holder 220 for attaching a blade (not shown) to the elongate handle. The scalpel 200 also includes a blade shield 230 that is removably attached to the elongate handle 210 and/or the blade holder 220 to protect the blade (not shown). In one or more embodiments, the elongate handle 210, blade holder 220 and/or the blade shield 230 may be formed from the recycled resin compositions described herein.

In one or more embodiments, medical devices formed from the recycled resin compositions described herein do not change color after being sterilized which may be measured in terms of yellowness index. For example, the medical devices may be sterilized, as described above, and undergo no change in color or appearance.

The medical devices may be formed using various methods known in the art. For example, such methods include injection molding, blow molding, extrusion and/or roto or rotational molding. Other methods known in the art may also be utilized to form the medical devices or components.

The medical devices formed from the recycled resin composition described may include a plunger rod that exhibits functional performance acceptable to users and/or clinicians.

In one or more embodiments, a plunger rod formed from the recycled resin compositions described above exhibit the same functional performance as plunger rods formed from non-recycled resin compositions or compositions that do not include any recycled content.

A third aspect of the present invention pertains to a method for forming medical devices and components. In one or more embodiments, the method includes providing a melt blend composition of the recycled resin compositions described herein. The method includes stabilizing the melt blend composition and solidifying the composition in a pre-selected shape, which may include a plunger rod, a syringe barrel, a catheter, a blood collection device, a surgical bland handle, a needle shield and a needle hub. In one or more embodiments, stabilizing the melt blend composition includes stabilizing the melt blend composition to withstand exposure to gamma rays, electron beams, X-ray radiation and ethylene oxide gas without compromising functional performance and/or aesthetic appeal of the finished product.

According to one embodiment, the step of providing a melt blend composition comprises feeding a recycled resin component and one or more of an antioxidant component, a slip additive component, an anti-static component, an impact modifier component, a colorant component, an acid scavenger component, a melt blend component, a clarifier component, a X-ray fluorescence agent component, a radio opaque filler component, a surface modifier component, a processing aid component and a reinforcing agent component into a melt compounding extruder. The step of solidifying the composition comprises one of injection molding the composition, extruding the composition and rotational molding the composition.

The recycled resin compositions, medical devices and components made from such compositions and the methods of making such medical devices and components provide a unique supply chain system which reduces the impact on landfills.

The present invention will be further understood by reference to the following non-limiting examples; however, the scope of the claims is not to be limited thereby.

EXAMPLES

The Inventive Formulations 1-6 were prepared by mechanically mixing recycled polypropylene resins with virgin polypropylene resins, wherein the virgin polypropylene resins further comprised of antioxidants, acid scavengers and melt-stabilizer.

Inventive Formulation 1 included 60% by weight of recycled polypropylene component A and 40% by weight of a virgin polypropylene component A. Virgin polypropylene component A included up to 0.8% by weight of an antioxidant component and a melt-stabilizer component and up to 0.3% by weight of an acid scavenger component.

Inventive Formulation 2 included 70% by weight of a recycled polypropylene component B and 30% by weight of virgin polypropylene component A, as described above.

Inventive Formulation 3 included 50% by weight of a recycled polypropylene component C and 50% by weight of a virgin polypropylene component A. as described above Inventive Formulation 4 included 60% by weight of recycled polypropylene component A and 40% by weight of a virgin polypropylene component B. Virgin polypropylene component B included up to 0.3% by weight of an antioxidant component and up to 0.2% by weight of an acid scavenger component.

Inventive Formulation 5 included 50% by weight of recycled polypropylene component B and 50% of virgin polypropylene component B, as described above.

Inventive Formulation 6 included 60% by weight of a recycled polypropylene component D and 40% by weight of virgin polypropylene component A, as described above.

The physical properties of each of Inventive Formulations 1-6 were analyzed. Specifically, the flexural modulus, tensile strength @ yield, tensile strength @ break, tensile elongation @ yield, tensile elongation @ break, tensile modulus, Izod impact strength and heat deflection temperature of Inventive Formulations 1-6 are evaluated and provided below in Table 1. For comparison, typical ranges for the physical properties of virgin polypropylene components are provided in Table 2.

The flexural modulus was measured according to ASTM D790-03. The tests were carried out on five specimens of each of the Inventive Formulations 1-6. The tests were carried out using a 0.05 in/min crosshead speed and a 2 inch support span length on an instrument provided by Instru-Met Corp., of Rahway, N.J., U.S.A. The specimens were formed using an injection molding process and conditioned at 23° C. and 50% relative humidity (RH) for 40 hours before the testing was performed. The average flexural modulus measurement of each of the five samples for Inventive Formulations is provided in Table 1.

The tensile properties of Inventive Formulations 1-6 were evaluated according to ASTM D638-03. The tests were carried out on five specimens of each of the Inventive Formulations 1-6. The tests were carried out using a crosshead speed of 2.0 in/min on an instrument provided by Instru-Met Corp., of Rahway, N.J., U.S.A. The type I tensile bar specimens were formed using an injection molding process and conditioned at 23° C. and 50% RH for 40 hours before the testing was performed. The average tensile strength @ yield, tensile strength @ break, tensile elongation @ yield, tensile elongation @ break and tensile modulus measurements of each of the five samples for Inventive Formulations is provided in Table 1.

The Izod impact strength of Inventive Formulations 1-6 were evaluated according to ASTM D256-02. The tests were carried out on ten specimens of each of the Inventive Formulations 1-6. The average Izod impact strength measurements for Inventive Formulations 1-6 are provided in Table 1.

The heat deflection temperature of Inventive Formulations 1-6 were evaluated according to ASTM D648-06 using an HDT/Vicat instrument available from Tinius Olsen, Inc. of Horsham, Pa., U.S.A. under a load of 66 psi. The average heat deflection temperature for Inventive Formulations 1-6 are provided in Table 1.

TABLE 1

Physical Properties of Inventive Formulations 1-6.

| | Inventive Formulation | | | | | |
|---|---|---|---|---|---|---|
| | 1 | 2 | 3 | 4 | 5 | 6 |
| Flexural Modulus (psi) | | | | | | |
| Average | 174345 | 148373 | 207247 | 187735 | 159857 | 157830 |
| Standard Deviation | 2153 | 1288 | 4749 | 4200 | 2629 | 1385 |
| Tensile Strength @ Yield (psi) | | | | | | |
| Average | 4694 | 4372 | 4959 | 4919 | 4737 | 4408 |
| Standard Deviation | 77 | 74 | 100 | 42 | 41 | 56 |
| Tensile Strength @ Break (psi) | | | | | | |
| Average | 2228 | 2665 | 4044 | 4058 | 2740 | 2798 |
| Standard Deviation | 304 | 81 | 779 | 162 | 81 | 84 |
| Tensile Elongation @ Yield (%) | | | | | | |
| Average | 9.67 | 11.1 | 8.37 | 7.87 | 9.27 | 8.41 |
| Standard Deviation | 0.750 | 0.558 | 0.255 | 0.515 | 0.436 | 0.939 |
| Tensile Elongation @ Break (psi) | | | | | | |
| Average | 116 | 254 | 24.8 | 23.2 | 165 | 241 |
| Standard Deviation | 141 | 121 | 15.3 | 3.50 | 40.5 | 62.3 |
| Tensile Modulus (psi) | | | | | | |
| Average | 238539 | 205376 | 264521 | 251694 | 234553 | 234458 |
| Standard Deviation | 7031 | 11233 | 6799 | 9940 | 11561 | 2841 |
| Izod Impact Strength (ft-lbs/in) | | | | | | |
| Average | 0.46 | 0.51 | 0.53 | 0.53 | 0.44 | 0.51 |
| Heat Deflection Temperature (° C.) | | | | | | |
| Average | 84.6 | 77.8 | 109.3 | 92.2 | 96.1 | 104.9 |

TABLE 2

Typical Physical properties of Virgin polyolefin resins.
Physical Properties

| | |
|---|---|
| Flexural Modulus | 145037.7 psi (1000 MPa)-290075.4 psi (2000 MPa) |
| Tensile strength @yield | 3625.9 psi (25 MPa)-6526.7 psi (45 MPa) |
| Tensile elongation @yield | 6%-15% |
| Tensile Modulus | 145037.7 psi (1000 MPa)-261067.9 psi (1800 MPa) |
| Notched Izod Impact Strength | 0.3 ft-lb/in-1.0 ft-lb/in |
| Heat Deflection Temperature | 70° C.-110° C. |

The physical properties of the Inventive Formulations 1-6 are comparable to the physical properties of virgin polyolefin resins, shown in Table 2. Accordingly, the recycled resin compositions described herein achieve the goals of utilizing recycled resins that are biocompatible and useful for medical device applications, without compromising the physical properties of the resulting devices.

Inventive Formulations 1-6 were also analyzed for biocompatibility. Specifically, each of Inventive Formulations 1-6 was analyzed in accordance with ANSI/AAMI/ISO 10-993-5 and the United States Pharmacopeia Biological Tests and Assays, Biological Reactivity Tests, in Vitro <87>. The United States Pharmacopeia Biological Reactivity Tests, in Vitro <87> are designed to determine the biological reactivity of mammalian cell cultures following contact with elastomeric plastics and other polymeric materials with direct or indirect patient contact or of specific extracts prepared from the materials under test. The elution test described in United States Pharmacopeia Biological Reactivity Tests, in Vitro <87> was carried out on Inventive Formulations 1-6.

Each of Inventive Formulations 1-6 passed or met the standard for the cytotoxicity tests with a United States Pharmacopeia score of zero, thereby meeting the criteria for preclinical toxicological safety evaluation established by United States Pharmacopeia and ISO 10-993-5. All of the biocompatibility tests were conducted in accordance with Good Laboratory Practice or GLP principles following procedures known in the art.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method for molding a medical device comprising:
providing a biocompatible recycled polypropylene resin composition sourced from a traceable source, wherein the recycled polypropylene resin composition comprises post-industrial recycled resin, post-consumer recycled resin and combinations thereof, the recycled polypropylene resin composition having a cytotoxicity score of zero;
mechanically mixing 50-70% by weight of the recycled polypropylene resin composition with 30 to 50% virgin polypropylene resin, the virgin polypropylene resin including 0.3% to 0.8% by weight of an anti-oxidant component and a melt-stabilizer component and 0.2% to 0.3% by weight of an acid scavenger component;
providing one or more of an slip additive component, anti-static component, impact modifier component, colorant component, x-ray fluorescence agent component, radio opaque filler component, surface modifier component, processing aid component, clarifier component, nucleating agents and reinforcing agent component;
forming a biocompatible, fluid path contact medical device using an injection molding process; and
conditioning the medical device at 23° C. and 50% relative humidity for 40 hours.

2. The method of claim 1, wherein the composition of recycled polypropylene resin composition mechanically mixed with virgin polypropylene resin comprises a flexural modulus in the range from about 70 kpsi to about 350 kpsi measured according to ASTM D790-03.

3. The method of claim 1, wherein the composition of recycled polypropylene resin composition mechanically mixed with virgin polypropylene resin comprises a heat deflection temperature from about 60° C. to 260° C.

4. The method of claim 1, wherein the composition of recycled polypropylene resin composition mechanically mixed with virgin polypropylene resin comprises a notched izod impact strength in the range from about 0.1 ft-lb/in to about 4.0 ft-lb/in.

5. The method of claim 1, wherein the composition of recycled polypropylene resin composition mechanically mixed with virgin polypropylene resin comprises 60% by weight of recycled polypropylene resin composition and 40% by weight of the virgin polypropylene resin.

6. The method of claim 1, wherein the composition of recycled polypropylene resin composition mechanically mixed with virgin polypropylene resin comprises 70% by weight of recycled polypropylene resin composition and 30% by weight of the virgin polypropylene resin.

7. The method of claim 1, wherein the composition of recycled polypropylene resin composition mechanically mixed with virgin polypropylene resin comprises 50% by weight of recycled polypropylene resin composition and 50% by weight of the virgin polypropylene resin.

* * * * *